United States Patent [19]

Liotta, Jr. et al.

[11] Patent Number: 5,166,370

[45] Date of Patent: Nov. 24, 1992

[54] PREPARATION OF TETRAHYDROFURAN USING A SUPPORTED TRANSITION METAL

[75] Inventors: Frank J. Liotta, Jr., Collegeville; Haven S. Kesling, Jr., Drexel Hill; Rangasamy Pitchai, West Chester, all of Pa.

[73] Assignee: Arco Chemical Technology, L.P., Wilmington, Del.

[21] Appl. No.: 684,407

[22] Filed: Apr. 12, 1991

[51] Int. Cl.$^5$ ............................................. C07D 307/08
[52] U.S. Cl. ..................................... 549/509; 568/862
[58] Field of Search ........................ 549/509; 568/862

[56] References Cited

U.S. PATENT DOCUMENTS

| | | | |
|---|---|---|---|
| 2,772,293 | 11/1956 | Gilbert et al. | 260/343.6 |
| 3,021,342 | 2/1962 | Manly | 260/345.1 |
| 3,467,679 | 9/1969 | Rogers | 260/346.1 |
| 3,859,369 | 1/1975 | Copelin | 260/635 R |
| 4,064,145 | 12/1977 | Taylor | 260/346.11 |
| 4,093,633 | 6/1978 | Tanabe et al. | 260/346.11 |
| 4,105,678 | 8/1978 | Taylor | 260/346.11 |
| 4,866,188 | 9/1989 | Scheben | 549/377 |

FOREIGN PATENT DOCUMENTS 1486379  9/1977  United Kingdom .

OTHER PUBLICATIONS

Hawley's Condensed Chemical Dictionary 11th Ed. (1987) p. 1170.

Primary Examiner—C. Warren Ivy
Assistant Examiner—A. A. Owens
Attorney, Agent, or Firm—Jonathan L. Schuchardt

[57] ABSTRACT

A process for producing tetrahydrofuran, 1,4-butanediol, and 2-methyl-1,3,-propanediol is disclosed. A mixture containing 4-hydroxybutanal and 3-hydroxy-2-methylpropanal is hydrogenated in the presence of a transition metal supported on a weakly acidic ion-exchange resin or zeolite-type material to give tetrahydrofuran as the major product, and 1,4-butanediol and 2-methyl-1,3-propanediol as minor products. High yields of 2-methyl-1,3-propanediol can be obtained.

26 Claims, No Drawings

PREPARATION OF TETRAHYDROFURAN USING A SUPPORTED TRANSITION METAL

FIELD OF THE INVENTION

The invention relates to the preparation of tetrahydrofuran. In particular, a mixture of 4-hydroxybutanal and 3-hydroxy-2-methylpropanal is hydrogenated in the presence of a supported transition metal catalyst to give tetrahydrofuran as the major product, and 1,4-butanediol and 2-methyl-1,3-propanediol as minor products.

BACKGROUND OF THE INVENTION

Tetrahydrofuran (THF), a widely used organic solvent and a starting material for the synthesis of poly(tetramethylene ether) glycols, can be produced by many well-known processes.

Catalytic hydrogenation of furan or maleic anhydride gives tetrahydrofuran, as disclosed in U.S. Pat. Nos. 2,772,293 and 3,021,342. Acid-catalyzed cyclodehydration of 1,4-butanediol in the presence of soluble acid catalysts is another well-known method of preparing THF.

A commercially important synthetic route to 1,4-butanediol involves hydroformylation of allyl alcohol in the presence of a rhodium catalyst to give a mixture of 4-hydroxybutanal (HBA) and 3-hydroxy-2-methylpropanal (HMPA). Catalytic hydrogenation of the aldehyde mixture under neutral conditions gives a mixture of 1,4-butanediol (BDO) and 2-methyl-1,3-propanediol (MPD). The 1,4-butanediol can then be cyclodehydrated under acid conditions to produce tetrahydrofuran. Alternatively, THF can be produced directly from 4-hydroxybutanal by hydrogenating the aldehyde mixture under acidic conditions, as disclosed in U.S. Pat. Nos. 4,064,145 and 4,105,678.

U.S. Pat. No. 4,105,678 teaches (Examples VI and VII) that an aqueous mixture of 4-hydroxybutanal and 3-hydroxy-2-methylpropanal can be hydrogenated with palladium on carbon in the presence of acetic acid at 114° C. to give a mixture of 1,4-butanediol, tetrahydrofuran, and 2-methyl-1,3-propanediol. 4-Hydroxybutanal was quantitatively converted to THF using palladium on carbon by increasing the reaction temperature to 190° C.

The processes described in U.S. Pat. Nos. 4,105,678 and 4,064,145 suffer from several disadvantages. The activity of palladium on carbon is insufficient for producing satisfactory yields of both THF and 2-methyl-1,3-propanediol. The use of soluble acids such as acetic acid results in low yields of 2-methyl-1,3-propanediol (less than 3%) because 3-hydroxy-2-methylpropanal dehydrates under the reaction conditions to give 1-propen-2-al (methacrolein), which subsequently polymerizes or is hydrogenated to give isobutyl alcohol. Soluble acids also catalyze undesirable aldol condensation reactions. Product isolation in the presence of soluble acids is difficult, and yield losses through dehydration and esterification reactions are significant. Recovery and reuse of soluble acids is impractical and uneconomical.

Thus, while an acid catalyst is needed to promote cyclodehydration of 4-hydroxybutanal, strongly acidic conditions promote unwanted dehydration of 3-hydroxy-2-methylpropanal, which results in low yields of 2-methyl-1,3-propanediol.

It is therefore an object of this invention to provide a process for producing tetrahydrofuran from 4-hydroxybutanal using a supported dehydration/hydrogenation catalyst to overcome the problems of soluble acid catalysts. It is also an object of the invention to improve the activity of the catalyst relative to the palladium-on-carbon system. A further object is to develop a THF process that gives good selectivity in the conversion of 3-hydroxy-2-methylpropanal to 2-methyl-1,3-propanediol.

SUMMARY OF THE INVENTION

The invention is a process for producing tetrahydrofuran, 1,4-butanediol, and 2-methyl-1,3-propanediol from a mixture of 1,4-hydroxybutanal and 3-hydroxy-2-methylpropanal. According to the process, a mixture of the aldehydes is hydrogenated in the presence of one or more transition metal compounds supported on a weakly acidic ion-exchange resin or a zeolite-type material to produce tetrahydrofuran as the major product and 1,4-butanediol and 2-methyl-1,3-propanediol as minor products.

DETAILED DESCRIPTION OF THE INVENTION

An aqueous mixture of 4-hydroxybutanal and 3-hydroxy-2-methylpropanal is preferably used as a starting material for producing tetrahydrofuran according to the process of the invention. Such a mixture is commonly obtained when allyl alcohol is hydroformylated using a rhodium catalyst as described, for example, in U.S. Pat. No. 4,064,145. The hydroformylation product is advantageously extracted with water to selectively separate 4-hydroxybutanal and 3-hydroxy-2-methylpropanal from other reaction components. The resulting aqueous aldehyde mixture may then be hydrogenated according to the process of this invention. The aqueous solution may have any desired concentration of aldehydes present. Typically, the amount of 4-hydroxybutanal present will be within the range of about 1 to about 50 weight percent based on the amount of water present. An aqueous mixture containing about 5 to about 15 weight percent of 4-hydroxybutanal is conveniently used. The concentration of 3-hydroxy-2-methylpropanal is typically within the range of about 0.2 to about 5.0 weight percent.

Although aqueous aldehyde mixtures are preferred, the process of the invention may be performed with non-aqueous mixtures. Thus, any mixture that contains 4-hydroxybutanal and water or an inert organic solvent may be used in the process. Hydroxylated solvents, such as aliphatic alcohols or aqueous mixtures containing aliphatic alcohols, are preferred. The most preferred solvent is water.

The process of the invention is performed in the presence of one or more transition metal compounds. "Transition metal compound" as defined herein is any compound that contains a transition element as defined in Hawley's Condensed Chemical Dictionary, 11th edition (1987), p. 1170. Thus, the transition elements are elements with atomic numbers 21-29, 39-47, 57-59, and all known elements with atomic numbers greater than 88. Preferred transition metal compounds contain a metal selected from the group consisting of platinum, palladium, silver, copper, vanadium, tungsten, cobalt, nickel, iron, rhenium, rhodium, ruthenium, manganese, chromium, molybdenum, iridium, and zirconium. Particularly preferred transition metal compounds are those that contain palladium, nickel, ruthenium, or iron.

The transition metal compound may be in the elemental state or may be in the form of a complex or salt that contains the metal. Transition metal salts are generally most suitable for the purpose of forming a supported catalyst, particularly with ion-exchange type supports. With zeolite-type supports, the elemental form of the transition metal compound will also be suitable. Suitable transition metal compounds include, but are not limited to, nitrates, halides, oxalates, oxides, sulfates, acetonylacetonates, tartrates, carbonyl complexes, amine complexes, and acetates of the above-mentioned transition metals. Examples of suitable compounds are palladium nitrate, palladium chloride, palladium acetate, tetraamine palladium nitrate, hexamine ruthenium nitrate, ruthenium acetate, nitrosoruthenium nitrate, vanadium chloride, platinum, platinum(II) chloride, rhenium, and the like. Mixtures of transition metal compounds may be used.

The transition metal catalysts used in the process of the invention are supported on either a weakly acidic ion-exchange resin or a zeolite-type material.

Although any acidic ion-exchange resin may be used, only weakly acidic ion-exchange resins are well-suited for use in the process. These resins are typically granular or spherical polymer particles having a polystyrene, acrylic, methacrylic, or phenolic matrix, and having either carboxylic acid or phosphonic acid active groups. The resins are produced either by condensation or addition polymerization. Preferably, the weakly acidic ion-exchange resin has carboxylic acid active groups. Examples of suitable resins include "Amberlite CG-50" and "Amberlite IR-64" resins (Products of Rohm and Haas Company), "Dowex CCR-1" and "Dowex CCR-2" resins (Products of Dow Chemical Company), and the like. Strongly acidic ion-exchange resins, such as those having sulfonic acid active groups, are generally much less suitable because they promote dehydration of 3-hydroxy-2-methylpropanal (resulting in low 2-methyl-1,3-propanediol yields) and also catalyze undesirable aldol condensation reactions of 4-hydroxybutanal.

Zeolite-type materials may also be used as the catalyst support. Preferably, the zeolite-type material has moderate acidity. Zeolites having high silica to alumina ratios are preferred. Preferred zeolite-type materials have a silica to alumina ratio greater than about 5. Particularly preferred are dealuminated Y-zeolites that have silica to alumina ratios greater than or equal to about 25. Examples of other suitable zeolite-type materials include mordenites such as "CBV10A," "CBV20A," and "CBV30A" mordenites (Products of Conteka), and Y-zeolites such as "Y-CBV400," "Y-CBV500," "Y-CBV610," "Y-CBV712," "Y-CBV720," and "Y-CBV760" zeolites (also Products of Conteka). More highly acidic zeolites such a "ZSM-5" zeolite (Product of Conteka) give high THF/BDO ratios, but are generally less satisfactory because they also promote aldol condensation reactions. It is also possible to use other weakly acidic catalyst supports including various clays, pillared clays, diatomaceous earth, and the like. The clays may be modified with mixed metal oxides to provide a suitable weakly acidic support medium for the hydrogenation catalyst.

The transition metal compound or compounds may be supported on weakly acidic ion-exchange resins by standard ion-exchange techniques. Typically, the ion-exchange resin is combined with an aqueous solution of the transition metal salt, the aqueous phase containing excess metal ions is separated from the supported transition metal catalyst and the resin is rinsed with water.

The transition metal compound or compounds may be supported on the zeolite-type supports using any of a number of techniques that are well known to those skilled in the art, including, for example, ion-exchange or incipient-wetness methods. The ion-exchange method generally provides catalysts with longer retention of activity. Zeolite catalysts made by the incipient-wetness technique generally give superior MPD yields. Using the incipient-wetness technique, the zeolite-type material is typically combined with a solution of the transition metal compound in a minimum amount of water, and the water is subsequently evaporated.

When more than one transition metal compound is used, the compounds may be deposited on the support simultaneously or stepwise in any order desired.

When a zeolite-supported catalyst is prepared, it is generally preferred to pre-activate the catalyst. Pre-activation is accomplished by calcining the supported transition metal catalyst, preferably at a temperature within the range of about 150° C. to about 500° C. Especially preferred are calcination temperatures within the range of about 350° C. to 500° C. Preferably, the catalyst is then reduced with hydrogen at a temperature within the range of about 100° C. to about 350° C., preferably 250° C. to 350° C. The calcination/reduction procedures may be performed using any suitable reaction vessel. A tube furnace is convenient for pre-activating multigram quantities of catalyst.

Catalysts suitable for use in a fixed-bed reactor can be prepared by extruding, spray-drying, or other methods known to those skilled in the art, a combination of supported catalyst and a binder such as clay or alumina to make pellets. Clay is preferred as a binder.

With the weakly acidic ion-exchange resin supports, the metal loading on the support is preferably within the range of about 0.1 and about 10 weight percent depending upon which resin is used and which method is used to prepare the catalyst.

With zeolite-type catalyst supports, the metal loading is preferably within the range of about 0.1 to about 20 weight percent, and like the ion-exchange resins, also depends upon which zeolite is used and which method is used to prepare the catalyst. A particularly preferred range is from about 1 to about 10 weight percent.

The process of the invention is performed under an atmosphere of hydrogen gas. Inert gases may be used, if desired, in combination with hydrogen. The process is preferably conducted under a pressure within the range of about 50 psig to about 2000 psig. More preferred is a pressure within the range of about 100 psig to about 1000 psig. Most preferred is the range from about 500 psig to about 750 psig.

The process of the invention may be performed at any desired temperature. It is preferred to perform the hydrogenation at a temperature within the range of about 25° C. to about 200° C. More preferred is the range from about 85° C. to about 150° C. Most preferred is the range from about 100° C. to about 125° C. When a weakly acidic ion-exchange resin is used as the support, it is especially preferred to use a temperature within the range of about 100° C. to about 125° C. The upper temperature limit useful for ion-exchange resin supports depends upon the decomposition temperature of the resin, and will typically be within the range of about 130° C. to about 150° C.

Increasing the temperature at which the process is performed usually increases the ratio of tetrahydrofuran to 1,4-butanediol obtained.

The process of the invention can be run batchwise or continuously, as desired. The supported catalyst system allows the process to be run using a fixed-bed, continuous process, and circumvents the problems associated with recovery and recycle of a soluble acid catalyst. The supported catalyst system also facilitates reaction product recovery from the aqueous solution. The zeolite-supported catalysts have high thermal stability and resist leaching and poisoning.

In one embodiment of the invention, 4-hydroxybutanal is hydrogenated using palladium supported on a weakly acidic ion-exchange resin. THF/1,4-butanediol ratios are typically high, and the solid acid is easily recovered and recycled. 2-methyl-1,3-propanediol yields are typically fairly low (5–10% at 100° C.), but still much higher than possible from the acetic acid process.

In a preferred embodiment of the invention, the hydrogenation is performed in the presence of palladium supported on a dealuminated Y-zeolite. The catalyst is preactivated by calcining and reducing with hydrogen. With this type of catalyst, 2-methyl-1,3-propanediol yields of 80% or better are possible at THF/1,4-butanediol ratios greater than 2.

In another preferred embodiment of the invention, the supported catalyst is a dealuminated Y-zeolite that contains two transition metal compounds: one of the transition metal compounds contains palladium, and the other transition metal compound contains a metal selected from the group consisting of nickel, ruthenium, iron, zinc, platinum, silver, and rhenium. Preferably, the transition metals are palladium and nickel. When the process of the invention is performed in the presence of the supported Pd/Ni catalyst, yields of 2-methyl-1,3-propanediol are 90–95% with maximum THF/1,4-butanediol product ratios of 1–2. Note that to get the highest yields of 2-methyl-1,3-propanediol it is necessary to settle for THF/1,4-butanediol ratios near unity.

The following examples merely illustrate the invention. Those skilled in the art will recognize many variations that are within the spirit of the invention and scope of the claims.

Sample Catalyst Preparation Procedures Preparation of Pd on Ion-Exchange Resins

The ion-exchange resin (25 g) was added slowly with stirring to a solution of tetraamine palladium nitrate (3.9 g) in water (100 mL). After 30–60 minutes of stirring, the solution was filtered, and the resin was washed with water (100 mL). The catalyst was dried overnight under vacuum at 110° C.

Calcination/reduction procedures: Zeolite-supported catalysts

The zeolite-supported catalysts were calcined by heating to the desired temperature in a tube furnace in the presence of air, and maintaining this temperature for two hours. The catalyst was cooled while maintaining the air flow. The catalyst was then reduced by heating the tube to the desired temperature in the presence of hydrogen for 4 hours. The reduced catalyst was cooled to room temperature under a stream of air. The calcination and reduction temperatures corresponding to various calcination/reduction procedures are listed below:

| Preparation of 5% Pd on Zeolite by Incipient Wetness | | |
|---|---|---|
| Procedure | Calcination Temp (°C.) | Reduction Temp (°C.) |
| A | 250 | 150 |
| B | 500 | 350 |
| C | 350 | 150 |
| D | 350 | 250 |
| E | 350 | 350 |

Conteka "CBV720" powdered Y-zeolite (50 g) was added to a solution of tetraamine palladium nitrate (7.7 g) in water (72 mL) and mixed to form a thick paste. The paste was dried under vacuum at 110° C. for 4 hours. Calcination/reduction procedure "A" was then used to activate the catalyst.

Preparation of Pd/Ni on Zeolite by Incipient Wetness

A solution of tetraamine palladium nitrate (7.7 g), nickel acetate hydrate (1.4 g), and water (72 mL) was prepared. Conteka "CBV720" powdered Y-zeolite was added and mixed to form a thick paste. The paste was oven-dried under vacuum at 110° C. for four hours. Calcination/reduction procedure "B" was then used to activate the catalyst.

Preparation of Palladium on Y-Zeolites by Ion Exchange

A 0.01M solution of tetraamine palladium nitrate (3.1 g) in water was prepared. This solution was added dropwise to a stirred suspension of powdered Conteka "CBV720" Y-zeolite (20 g) in water (2500 mL). The resulting suspension was stirred for 24 to 48 hours at ambient temperature. The suspension was filtered, and the zeolite was oven-dried under vacuum at 110° C. for four hours. Calcination/reduction procedure "E" was then used to activate the catalyst.

Preparation of Nickel on Y-Zeolites by Ion Exchange

A 0.01M aqueous solution of nickel acetate tetrahydrate (3.2 g) in water was prepared. This solution was added dropwise to a stirring suspension of powdered Conteka "CBV720" Y-zeolite (15 g) in water (2500 mL). The suspension was stirred for 48 hours at room temperature. After filtration, the zeolite was oven-dried under vacuum at 110° C. for four hours. Calcination/reduction procedure "C" was then used to activate the catalyst.

Preparation of Fe/Pd on Y-Zeolite by Ion Exchange

A suspension of Conteka "CBV720" Y-zeolite (35.0 g) in water (3500 mL) was prepared, and the pH was adjusted to 3.9 with 1M sulfuric acid. A solution of iron sulfate heptahydrate (8.75 g) in water (500 mL) was added dropwise to the stirred suspension. After stirring for two days at ambient temperature, the mixture was filtered. The product was dried at 120° C. under vacuum for 4 hours.

A suspension of the zeolite-supported iron catalyst prepared above (15 g) in water (3000 mL) was prepared. A solution of tetraamine palladium nitrate (2.95 g) in water (800 mL) was added dropwise to the stirred suspension. After stirring for 1 day, the mixture was filtered, and the precipitate was dried at 120° C. under vacuum for 4 hours. Calcination/reduction procedure "B" was then used to activate the catalyst.

EXAMPLES 1-5

Preparation of THF using Transition Metals Supported on Weakly Acidic Ion-Exchange Resins An aqueous solution containing 4-hydroxybutanal (HBA) (11%) and 3-hydroxy-2-methylpropanal (1.2%) was hydrogenated under 1000 psig of hydrogen in a stirred, stainless-steel autoclave reactor. The results of several runs are summarized in Table 1. As shown in Comparative Example 1 (Table 1), almost none of the 3-hydroxy-2-methylpropanal initially present was converted to 2-methyl-1,3-propanediol when the soluble acetic acid catalyst system of the prior art was used. 2-methyl-1,3-propanediol yields in the 5-10% range were observed with the ion-exchange resin supported catalysts of the invention; selectivities to THF or 1,4-butanediol were typically greater than 90%.

TABLE 1

Preparation of THF using Palladium Supported on a Weakly Acidic Ion-Exchange Resin

| Ex # | Catalyst System | Cat. (g) | Temp. (°C.) | Time (min.) | % Conv. HBA | % Conv. HMPA | THF/BDO (m/m) | % Sel. THF/BDO | % MPD Yield |
|---|---|---|---|---|---|---|---|---|---|
| C1 | 5% Pd/C, HOAc (20 g) | 1.2 | 140 | 120 | 72 | 98 | >100 | 58 | <1 |
| 2 | 1.4% Pd on IR-64 | 5.0 | 140 | 120 | 55 | 98 | 12 | 98 | 5 |
| 3 | 1.4% Pd on CG-50 | 5.0 | 140 | 120 | 22 | 98 | 58 | 90 | 5 |
| 4 | 1.4% Pd on IR-64 | 5.0 | 100 | 120 | 57 | 98 | 12 | 92 | 10 |
| 5 | 1.4% Pd on CG-50 | 15 | 100 | 30 | 36 | 98 | 18 | 67 | 5 |

IR-64 = "AMBERLITE IR-64" resin; CG-50 = "AMBERLITE CG-50" (Rohm and Haas Company); HBA = 4-hydroxybutanal; HMPA = 3-hydroxy-2-methylpropanal; THF = tetrahydrofuran; BDO = 1,4-butanediol; MPD = 2-methyl-1,3-propanediol
THF/BDO (m/m) is the observed mole ratio of THF to 1,4-butanediol.
% Sel THF/BDO is the percent selectivity in the conversion of HBA to THF or BDO.
MPD % yield is calculated based on the amount of HMPA initially present.

EXAMPLES 6-12

Preparation of THF using Transition Metals Supported on a Zeolite-type Material An aqueous solution (200 g) containing 4-hydroxybutanal (HBA) (11%) and 3-hydroxy-2-methylpropanal (1.2%) was hydrogenated under 1000 psig of hydrogen in a stirred, stainless-steel autoclave reactor. The results of several runs are summarized in Table 2. The results illustrate the dependence of product ratios and selectivites on catalyst preparation and activation procedures. As shown by Example 7, 2-methyl-1,3-propanediol yields as high as 96% can be achieved if the incipient-wetness method of catalyst preparation is employed; THF/1,4-butanediol ratios approach unity when high 2-methyl-1,3-propanediol yields are obtained.

TABLE 2

Preparation of THF using Palladium Supported on a Zeolite-type Material

| Ex # | Catalyst System | Cat. (g) | Temp. (°C.) | Time (min.) | % Conv. HBA | % Conv. HMPA | THF/BDO (m/m) | % Sel. THF/BDO | % MPD Yield |
|---|---|---|---|---|---|---|---|---|---|
| C1 | 5% Pd/C, HOAc (20 g) | 1.2 | 140 | 120 | 72 | 98 | 50 | 58 | <1 |
| C6 | 4.0% Pd/ZSM-5 (W)_* | 5.0 | 140 | 60 | 55 | 99 | 20 | 85 | 5 |
| 7 | 4.3% Pd/CBV-720 (C/W) | 5.0 | 100 | 60 | 99 | 97 | 1.1 | 99 | 96 |
| 8 | 4.3% Pd/CBV-760 (A/W) | 5.0 | 100 | 60 | 99 | 99 | 1.2 | 99 | 79 |
| 9 | 2.0% Pd/CBV-720 (B/E) | 5.0 | 100 | 60 | 98 | 96 | 6.3 | 90 | 15 |
| 10 | 2.0% Pd/CBV-720 (C/E) | 5.0 | 100 | 60 | 91 | 93 | 54 | 99 | 5 |
| 11 | 3.5% Pd/CBV-720 (B/W) | 5.0 | 100 | 60 | 90 | 77 | 58 | 85 | 5 |
| 12 | 4.0% Pd/CBV-10A | 5.0 | 100 | 60 | 77 | 77 | 31 | 77 | 13 |

"ZSM-5", "CBV-720", and "CBV-760" zeolites and "CBV-10A" mordenite are products of Conteka.
Catalyst preparation: W = incipient wetness method; E = ion exchange method.
Catalyst activation: A = calcined at 250° C., reduced at 150° C.; B = calcined at 500° C., reduced at 350° C.; C = calcined at 350° C., reduced at 150° C..
HBA = 4-hydroxybutanal; HMPA = 3-hydroxy-2-methylpropanal; THF = tetrahydrofuran; BDO = 1,4-butanediol; MPD = 2-methyl-1,3-propanediol.
THF/BDO (m/m) is the observed mole ratio of THF to 1,4-butanediol.
% Sel THF/BDO is the percent selectivity in the conversion of HBA to THF or BDO.
MPD % yield is calculated based on the amount of HMPA initially present.
*Calcined at 350° C.

EXAMPLES 13-21

Preparation of THF using a Bimetallic Transition Metal Catalyst Supported on a Zeolite-Type Material An aqueous solution (200 g) containing 4-hydroxybutanal (HBA) (11%) and 3-hydroxy-2-methylpropanal (1.2%) was hydrogenated under 1000 psig of hydrogen in a stirred, stainless-steel autoclave reactor. The results of several runs are summarized in Table 3. Bimetallic systems typically give high 2-methyl-1,3-propanediol yields. If THF/1,4-butanediol ratios close to unity are acceptable, a Ni-Pd combination can be used to give an almost quantitative 2-methyl-1,3-propanediol yield (see Example 20).

TABLE 3

Preparation of THF using Transition Metals Supported on a Zeolite-type Material

| Ex # | Catalyst System | Cat. (g) | Temp. (°C.) | Time (min.) | % Conv. HBA | % Conv. HMPA | THF/BDO (m/m) | % Sel. THF/BDO | % MPD Yield |
|---|---|---|---|---|---|---|---|---|---|
| C1 | 5% Pd/C, HOAc (20 g) | 1.2 | 140 | 120 | 72 | 98 | 50 | 58 | <1 |
| 13 | 2% Pd (B/E) | 5.0 | 100 | 60 | 98 | 96 | 6.3 | 90 | 15 |

TABLE 3-continued

Preparation of THF using Transition Metals Supported on a Zeolite-type Material

| Ex # | Catalyst System | Cat. (g) | Temp. (°C.) | Time (min.) | % Conv. HBA | % Conv. HMPA | THF/BDO (m/m) | % Sel. THF/BDO | % MPD Yield |
|---|---|---|---|---|---|---|---|---|---|
| 14 | 0.6% Fe/2.8% Pd (B/E) | 5.0 | 100 | 60 | 99 | 98 | 8.3 | 95 | 26 |
| 15 | 0.9% Ru/0.9% Pd (A/E) | 5.0 | 100 | 60 | 99 | 99 | 0.1 | 85 | 61 |
| 16 | 0.9% Ru/1.9% Pd (E) | 5.0 | 100 | 60 | 99 | 95 | 10 | 87 | 42 |
| 17 | 1.3% Ru/2.4% Pd (C/E) | 5.0 | 100 | 60 | 99 | 99 | 3.1 | 99 | 80 |
| 18 | 2.1% Ni/3.7% Pd (B/W) | 5.0 | 100 | 60 | 90 | 93 | 0.5 | 99 | 99 |
| 19 | 0.6% Ni/4.0% Pd (B/W) | 5.0 | 100 | 60 | 99 | 99 | 1.8 | 99 | 70 |
| 20 | 0.6% Ni/4.0% Pd (C/W) | 5.0 | 100 | 60 | 98 | 97 | 1.1 | 95 | 99 |
| 21 | 1.7% Ni/2.1% Pd (C/W) | 5.0 | 100 | 60 | 62 | 93 | 0.1 | 91 | 59 |

"Y-CBV720" zeolite was the support used for Examples 12–19; "Y-CBV760" zeolite was used for Example 20; both are products of Conteka.
Catalyst preparation: W = incipient wetness method; E = ion exchange method.
Catalyst activation: A = calcined at 250° C., reduced at 150° C.; B = calcined at 500° C., reduced at 350° C.; C = calcined at 350° C., reduced at 150° C..
HBA = 4 - hydroxybutanal; HMPA = 3-hydroxy-2-methylpropanal; THF = tetrahydrofuran; BDO = 1,4-butanediol; MPD = 2-methyl-1,3-propanediol.
THF/BDO (m/m) is the observed mole ratio of THF to 1,4-butanediol.
% Sel THF/BDO is the percent selectivity in the conversin of HBA to THF to BDO.
MPD % yield is calculated based on the amount of HMPA initially present.

We claim:

1. A process for producing tetrahydrofuran, 1,4-butanediol, and 2-methyl-1,3-propanediol, said process comprising:
hydrogenating 4-hydroxybutanal and 3-hydroxy-2-methylpropananl in the presence of one or more supported transition metal compounds, in which the catalyst support is selected from the group consisting of weakly acidic ion-exchange resins and zeolite-type materials, to produce tetrahydrofuran as the major product, and 1,4-butanediol and 2-methyl-1,3-propanediol as minor products.

2. The process of claim 1 wherein the transition metal compound contains a metal selected from the group consisting of platinum, palladium, silver, copper, vanadium, tungsten, cobalt, nickel, iron, rhenium, ruthenium, rhodium, manganese, chromium, molybdenum, iridium, and zirconium.

3. The process of claim 1 wherein the transition metal compound contains palladium.

4. The process of claim 1 wherein two transition metals are present: one transition metal compound contains palladium, and the other transition metal compound contains a metal selected from the group consisting of nickel, ruthenium, iron, zinc, platinum, silver, and rhenium.

5. The process of claim 1 wherein the catalyst support is a weakly acidic ion-exchange resin having carboxylic acid residues.

6. The process of claim 1 wherein the catalyst support is a zeolite-type material selected from mordenites and dealuminated zeolites.

7. The process of claim 1 wherein the catalyst is prepared by (a) calcining the transition metal compound and the catalyst support, and (b) reducing the catalyst with hydrogen.

8. The process of claim 1 wherein the process is performed at a temperature within the range of about 25° C. to about 200° C.

9. The process of claim 1 wherein the process is performed at a hydrogen pressure within the range of about 50 to 2000 psi.

10. The process of claim 1 wherein an aqueous solution containing the aldehydes is used for the hydrogenation.

11. A process for producing tetrahydrofuran, 1,4-butanediol, and 2-methyl-1,3-propanediol, said process comprising:
hydrogenating an aqueous solution containing 4-hydroxybutanal and 3-hydroxy-2-methylpropanal in the presence of at least one supported transition metal compound, in which the catalyst support is a zeolite-type material, to produce tetrahydrofuran as the major product, and 1,4-butanediol and 2-methyl-1,3-propanediol as minor products.

12. The process of claim 11 wherein the transition metal compound contains a metal selected from the group consisting of platinum, palladium, silver, copper, vanadium, tungsten, cobalt, nickel, iron, rhenium, ruthenium, rhodium, manganese, chromium, molybdenum, iridium, and zirconium.

13. The process of claim 11 wherein the transition metal compound contains palladium.

14. The process of claim 11 wherein two transition metal compounds are present: one transition metal compound contains palladium, and the other transition metal compound contains a metal selected from the group consisting of nickel, ruthenium, iron, zinc, platinum, silver, and rhenium.

15. The process of claim 11 wherein the zeolite-type catalyst support is selected from mordenites and dealuminated zeolites.

16. The process of claim 11 wherein the catalyst support is a dealuminated Y-zeolite having a silica to alumina ratio greater than about 5.

17. The process of claim 11 wherein the catalyst is prepared by (a) calcining the transition metal compound and the catalyst support at a temperature within the range of about 150° C. to about 500° C., and (b) reducing the catalyst with hydrogen at a temperature within the range of about 100° C. to about 350° C.

18. The process of claim 11 wherein the process is performed at a temperature within the range of about 25° C. to about 200° C.

19. The process of claim 11 wherein the process is performed at a hydrogen pressure within the range of about 50 to 2000 psi.

20. A process for producing tetrahydrofuran, 1,4-butanediol, and 2-methyl-1,3-propanediol, said process comprising:
hydrogenating an aqueous solution containing 4-hydroxybutanal and 3-hydroxy-2-methylpropanal in the presence of a palladium compound supported on a zeolite-type catalyst support to produce tetrahydrofuran as the major product, and 1,4-butanediol and 2-methyl-1,3-propanediol as the minor products.

21. The process of claim 20 wherein two transition metal compounds are present: one of the transition metal compounds is a palladium compound, and the other transition metal compound contains a metal selected from the group consisting of nickel, ruthenium, iron, zinc, platinum, silver, and rhenium.

22. The process of claim 20 wherein the zeolite-type catalyst support is a dealuminated zeolite.

23. The process of claim 20 wherein the dealuminated zeolite is a dealuminated Y-zeolite having a silica to alumina ratio greater than about 5.

24. The process of claim 20 wherein the catalyst is prepared by (a) calcining the palladium compound and the zeolite at a temperature within the range of about 150° C. to about 500° C., and (b) reducing the catalyst with hydrogen at a temperature within the range of about 100° C. to about 350° C.

25. The process of claim 20 wherein the process is performed at a temperature within the range of about 25° C. to about 200° C.

26. The process of claim 20 wherein the process is performed at a hydrogen pressure within the range of about 50 to 2000 psi.

* * * * *